US012573033B2

(12) United States Patent
Godrich et al.

(10) Patent No.: US 12,573,033 B2
(45) Date of Patent: Mar. 10, 2026

(54) SYSTEMS AND METHODS FOR PROCESSING ELECTRONIC IMAGES USING UNCERTAINTY ESTIMATION

(71) Applicant: PAIGE.AI, Inc., New York, NY (US)

(72) Inventors: Ran Godrich, New York, NY (US); Christopher Kanan, Pittsford, NY (US); Siqi Liu, New York, NY (US)

(73) Assignee: Paige.AI, Inc., New York, NY (US)

( * ) Notice: Subject to any disclaimer, the term of this patent is extended or adjusted under 35 U.S.C. 154(b) by 492 days.

(21) Appl. No.: 18/152,305

(22) Filed: Jan. 10, 2023

(65) Prior Publication Data

US 2023/0222653 A1    Jul. 13, 2023

Related U.S. Application Data

(60) Provisional application No. 63/298,740, filed on Jan. 12, 2022.

(51) Int. Cl.
*G06T 7/00*　　　　(2017.01)
*G16B 20/00*　　　 (2019.01)
*G16B 40/00*　　　 (2019.01)

(52) U.S. Cl.
CPC ............ *G06T 7/0012* (2013.01); *G16B 20/00* (2019.02); *G16B 40/00* (2019.02); *G06T 2207/10056* (2013.01); *G06T 2207/20081* (2013.01)

(58) Field of Classification Search
None
See application file for complete search history.

(56) References Cited

U.S. PATENT DOCUMENTS

2020/0160032 A1*　5/2020　Allen ...................... G06N 3/045
2020/0364587 A1*　11/2020　Kapur ...................... G06N 3/09

OTHER PUBLICATIONS

Pocevičiūtė, Milda, et al. "Can uncertainty boost the reliability of AI-based diagnostic methods in digital pathology?." arXiv preprint arXiv:2112.09693, Dec. 17, 2021.
Are open set classification methods effective on large-scale datasets? (plos.org) "Are open set classification methods effective on large-scale datasets?" by Ryne Roady, Tyler L. Hayes, Ronald Kemker, Ayesha Gonzales, and Christopher Kanan, published Sep. 4, 2020.
"Out-of-Distribution Detector for Neural Networks," Yen-Chang Hsu, Yilin Shen, Hongxia Jin, Zsolt Kira, https://arxiv.org/abs/2002.11297, Feb. 26, 2020.

* cited by examiner

*Primary Examiner* — Andrew H Lam
(74) *Attorney, Agent, or Firm* — Bookoff McAndrews, PLLC

(57)　　　ABSTRACT

A method for processing electronic images using uncertainty estimation may be used to determine whether to use an artificial intelligence (AI) assisted prediction. The method may include receiving one or more electronic images associated with a pathology specimen and providing the one or more electronic images to a machine learning model. The machine learning model may perform operations including determining a certainty level corresponding to a certainty that a predetermined AI system will provide an accurate prediction, determining whether the certainty level equals or exceeds a predetermined confidence threshold, and, upon determining that the certainty level does not equal or exceed a predetermined confidence threshold, determining to not use the predetermined AI system.

20 Claims, 11 Drawing Sheets

300

302 — RECEIVING A PLURALITY OF WHOLE SLIDE IMAGES

304 — PARTITIONING  EACH RECEIVED WHOLE SLIDE
IMAGE INTO FOREGROUND TILES

306 — EXTRACTING A VECTOR OF FEATURES FROM
EACH FOREGROUND TILE

308 — TRAINING A CLASSIFIER TO AGGREGATE THE VECTORS OF EACH
WHOLE SLIDE IMAGE AND CLASSIFY EACH WHOLE SLIDE IMAGE
AS ANY KNOWN LABELS OR AN UNKNOWN LABEL

310 — ASSIGNING A LABEL FOR EACH SLIDE

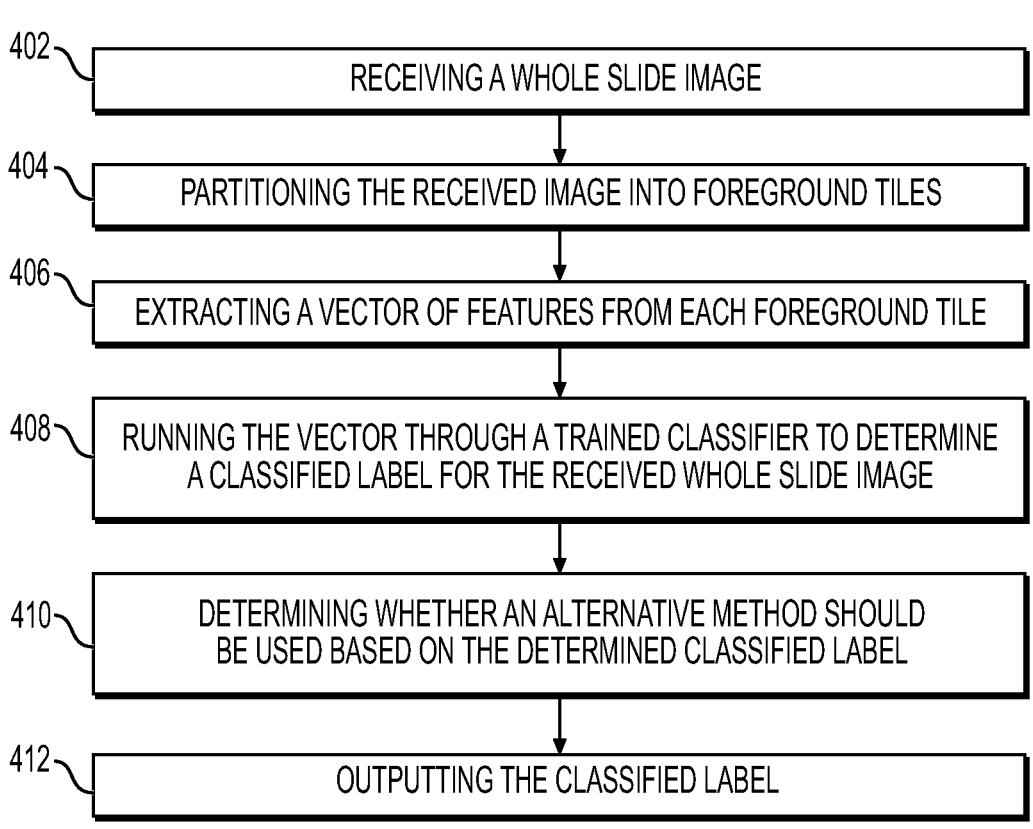

400

402 — RECEIVING A WHOLE SLIDE IMAGE

404 — PARTITIONING THE RECEIVED IMAGE INTO FOREGROUND TILES

406 — EXTRACTING A VECTOR OF FEATURES FROM EACH FOREGROUND TILE

408 — RUNNING THE VECTOR THROUGH A TRAINED CLASSIFIER TO DETERMINE A CLASSIFIED LABEL FOR THE RECEIVED WHOLE SLIDE IMAGE

410 — DETERMINING WHETHER AN ALTERNATIVE METHOD SHOULD BE USED BASED ON THE DETERMINED CLASSIFIED LABEL

412 — OUTPUTTING THE CLASSIFIED LABEL

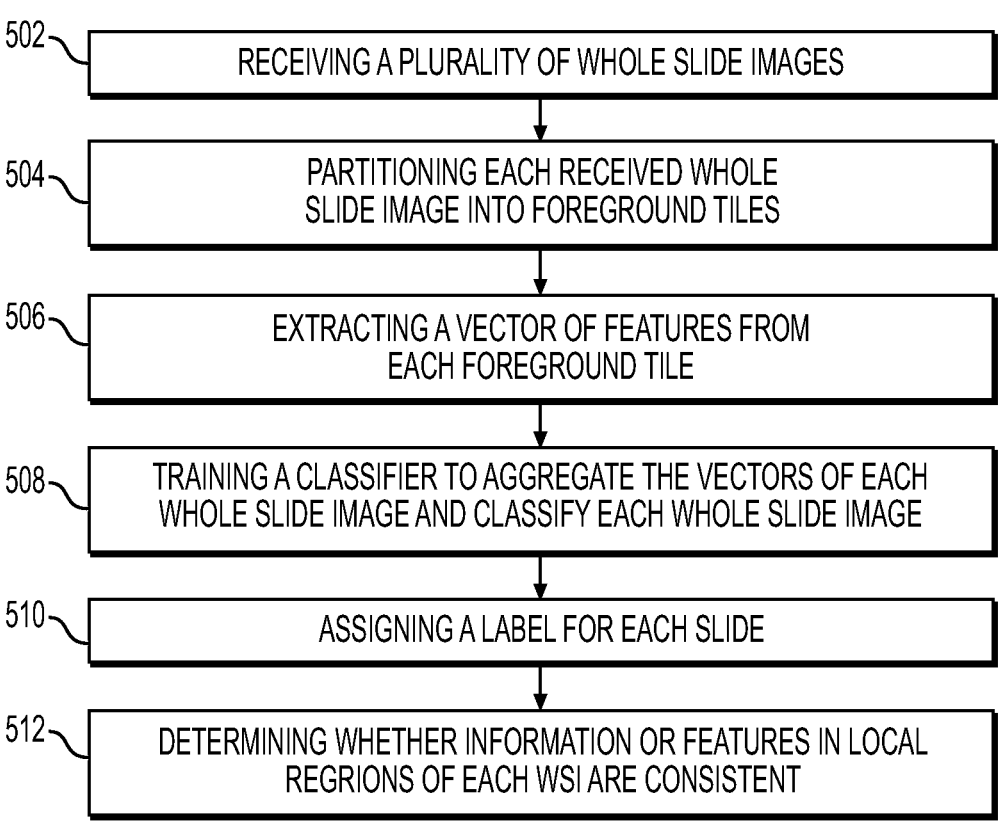

502 — RECEIVING A PLURALITY OF WHOLE SLIDE IMAGES

504 — PARTITIONING EACH RECEIVED WHOLE SLIDE IMAGE INTO FOREGROUND TILES

506 — EXTRACTING A VECTOR OF FEATURES FROM EACH FOREGROUND TILE

508 — TRAINING A CLASSIFIER TO AGGREGATE THE VECTORS OF EACH WHOLE SLIDE IMAGE AND CLASSIFY EACH WHOLE SLIDE IMAGE

510 — ASSIGNING A LABEL FOR EACH SLIDE

512 — DETERMINING WHETHER INFORMATION OR FEATURES IN LOCAL REGRIONS OF EACH WSI ARE CONSISTENT

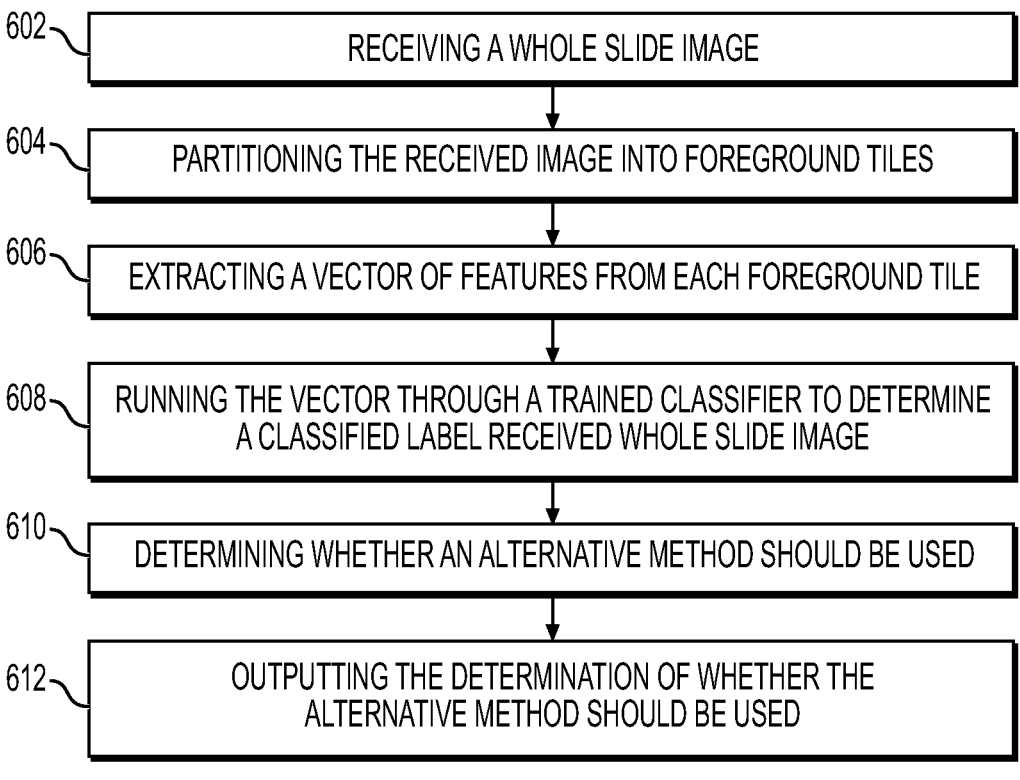

602 — RECEIVING A WHOLE SLIDE IMAGE

604 — PARTITIONING THE RECEIVED IMAGE INTO FOREGROUND TILES

606 — EXTRACTING A VECTOR OF FEATURES FROM EACH FOREGROUND TILE

608 — RUNNING THE VECTOR THROUGH A TRAINED CLASSIFIER TO DETERMINE A CLASSIFIED LABEL RECEIVED WHOLE SLIDE IMAGE

610 — DETERMINING WHETHER AN ALTERNATIVE METHOD SHOULD BE USED

612 — OUTPUTTING THE DETERMINATION OF WHETHER THE ALTERNATIVE METHOD SHOULD BE USED

702 — RECEIVING A PLURALITY OF WHOLE SLIDE IMAGES

704 — IDENTIFYING A SUBPOPULATION FOR EACH WHOLE SLIDE IMAGE AND AN ASSOCIATED CERTAINTY LEVEL

706 — TRAINING A CLASSIFIER TO TAKE, AS INPUT, A WHOLE SLIDE IMAGE AND DETERMINE, AS OUTPUT, A SUBPOPULATION AND/OR CERTAINTY LEVEL FOR THE RECEIVED WHOLE SLIDE IMAGE

800

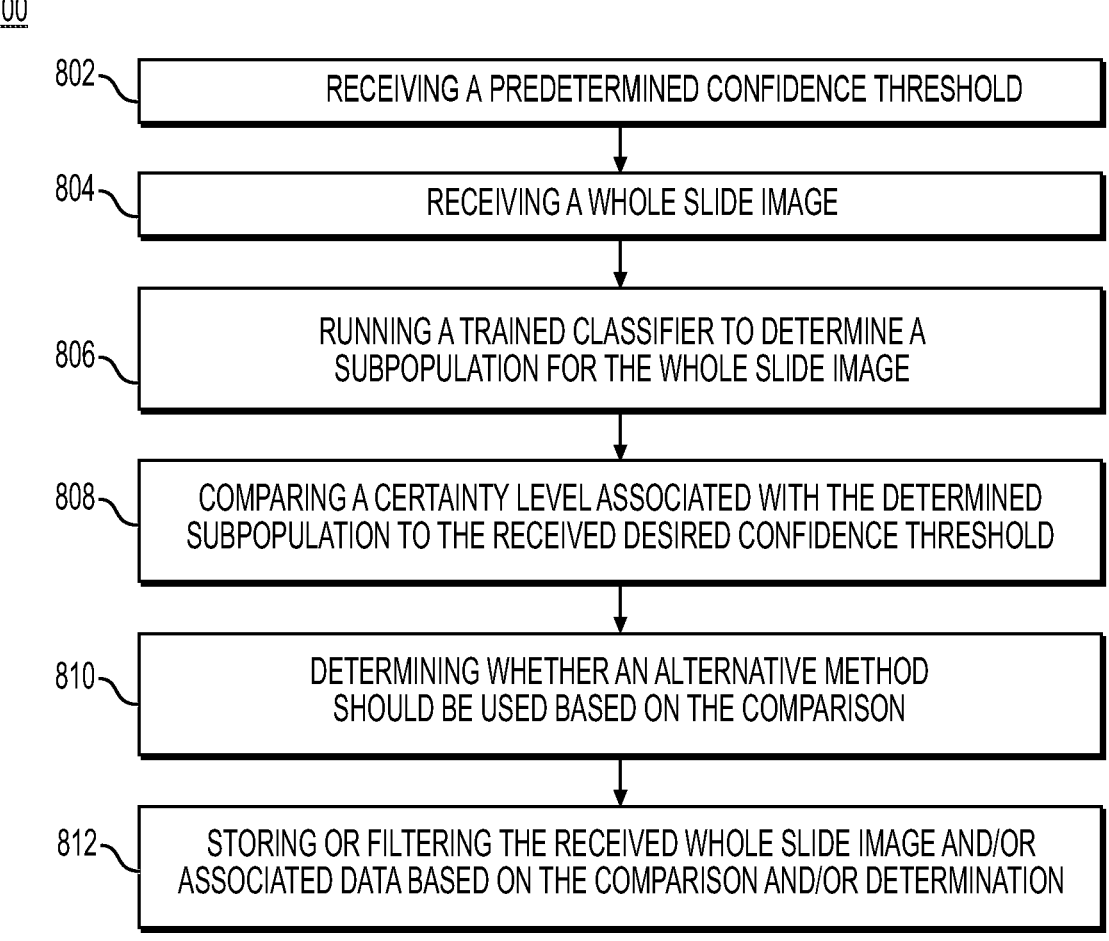

802 — RECEIVING A PREDETERMINED CONFIDENCE THRESHOLD

804 — RECEIVING A WHOLE SLIDE IMAGE

806 — RUNNING A TRAINED CLASSIFIER TO DETERMINE A SUBPOPULATION FOR THE WHOLE SLIDE IMAGE

808 — COMPARING A CERTAINTY LEVEL ASSOCIATED WITH THE DETERMINED SUBPOPULATION TO THE RECEIVED DESIRED CONFIDENCE THRESHOLD

810 — DETERMINING WHETHER AN ALTERNATIVE METHOD SHOULD BE USED BASED ON THE COMPARISON

812 — STORING OR FILTERING THE RECEIVED WHOLE SLIDE IMAGE AND/OR ASSOCIATED DATA BASED ON THE COMPARISON AND/OR DETERMINATION

*FIG. 8*

SYSTEMS AND METHODS FOR PROCESSING ELECTRONIC IMAGES USING UNCERTAINTY ESTIMATION

RELATED APPLICATION(S)

This application claims priority to U.S. Provisional Application No. 63/298,740 filed Jan. 12, 2022, the entire disclosure of which is hereby incorporated herein by reference in its entirety.

FIELD OF THE DISCLOSURE

Various embodiments of the present disclosure pertain generally to image processing methods. More specifically, particular embodiments of the present disclosure relate to systems and methods to process electronic images using uncertainty estimation.

BACKGROUND

Pre-existing or traditional tests (e.g., a polymerase chain reaction (PCR) test) may use inputs, such as human saliva, tissue, blood, etc., and output certain determinations (e.g., whether a person has coronavirus or COVID). However, these tests may fail if provided to a machine learning solution for processing.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for process electronic images using uncertainty estimation.

A method for processing electronic images using uncertainty estimation may be used to determine whether to use an artificial intelligence (AI) assisted prediction. The method may include receiving one or more electronic images associated with a pathology specimen and providing the one or more electronic images to a machine learning model. The machine learning model may perform operations including determining a certainty level corresponding to a certainty that a predetermined AI system will provide an accurate prediction, determining whether the certainty level equals or exceeds a predetermined confidence threshold, and, upon determining that the certainty level does not equal or exceed a predetermined confidence threshold, determining to not use the predetermined AI system.

Running the machine learning model to determine the certainty level may include identifying a subpopulation of the pathology specimen.

Running the machine learning model to determine whether the certainty level may include running a trained classifier to determine a classified label. The classified label may indicate at least one of a subpopulation or whether the pathology specimen is outside of the one or more predetermined subpopulations. Running the classifier to determine the classified label may include partitioning the received electronic image into a plurality of foreground tiles, extracting a vector of features from each foreground tile, and running each vector through the trained classifier to determine the classified label.

Running the machine learning model to determine whether the certainty level may include detecting one or more features in the received electronic image and determining a consistency of the detected one or more features.

Detecting the one or more features in the received electronic image and determining the consistency may include partitioning the received electronic image into a plurality of foreground tiles, extracting a vector of the detected one or more features from each foreground tile, determining local feature information for each foreground tile, and analyzing, using statistical analysis, the determined local feature information for all foreground tiles to determine the consistency.

The method may include outputting a visualization of the detected one or more features and/or the determined consistency.

Running the machine learning model to determine the certainty level may include partitioning the received electronic image into a plurality of foreground tiles, extracting a vector of features from each foreground tile, and running each extracted vector through the machine learning model to determine at least one of: (i) a subpopulation for the pathology specimen, or (ii) an unknown label indicating that the pathology specimen is outside the one or more predetermined subpopulations.

Determining to not use the predetermined AI system may include detecting that the pathology specimen is outside the one or more predetermined subpopulations.

The method may include determining that an alternative method should be used. The predetermined AI system may have been trained using results from the alternative method as ground truth.

The method may include determining the predetermined confidence threshold based on a user input. The certainty level may be based on a comparison of a performance by the predetermined AI system with a comparison of an alternative method.

The predetermined confidence threshold may be based on a certainty level associated with an alternative method. The predetermined AI system may be configured to detect a presence and/or an intensity of HER2 expression.

The predetermined AI system may be configured to predict a response to a polymerase chain reaction (PCR) test. The method may include outputting a recommendation for an alternative method. The alternative method may be configured to make a same type of prediction as the predetermined AI system.

The method may include storing or removing the received electronic image, based on whether the pathology specimen belongs to one or more predetermined subpopulations, to create a data set based on one or more electronic images for which the certainty level equals or exceeds the predetermined confidence threshold.

Aspects disclosed herein may provide a system for determining whether to use an artificial intelligence (AI) assisted prediction. The system may include at least one memory storing instructions, and at least one processor configured to execute the instructions to perform operations. The operations may include receiving one or more electronic images associated with a pathology specimen and providing the one or more electronic images to a machine learning model. The machine learning model may perform operations including determining a certainty level corresponding to a certainty that a predetermined AI system will provide an accurate prediction, determining whether the certainty level equals or exceeds a predetermined confidence threshold, and upon determining that the certainty level does not equal or exceed a predetermined confidence threshold determining to not use the predetermined AI system.

Running the machine learning model to determine the certainty level may include identifying a subpopulation of the pathology specimen.

Aspects disclosed herein may provide a non-transitory computer-readable medium storing instructions that, when executed by a processor, perform a method for identifying attributes of electronic images and displaying the attributes. The method may include receiving one or more electronic images associated with a pathology specimen and providing the one or more electronic images to a machine learning model. The machine learning model may perform operations including determining a certainty level corresponding to a certainty that a predetermined AI system will provide an accurate prediction, determining whether the certainty level equals or exceeds a predetermined confidence threshold, and upon determining that the certainty level does not equal or exceed a predetermined confidence threshold, determining to not use the predetermined AI system.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 4 illustrates a method of using the trained model or classifier of FIG. 3.

FIG. 5 illustrates a method of training a model or classifier using feature consistency to determine whether to use an AI-based approach, according to an exemplary embodiment of the present disclosure.

FIG. 6 illustrates a method of using the model or classifier of FIG. 5.

FIG. 8 illustrates a method of determining whether to use an AI-based approach based on an identified subpopulation and/or a predetermined confidence threshold, according to an exemplary embodiment of the present disclosure.

DESCRIPTION OF THE EMBODIMENTS

Figure 1A:
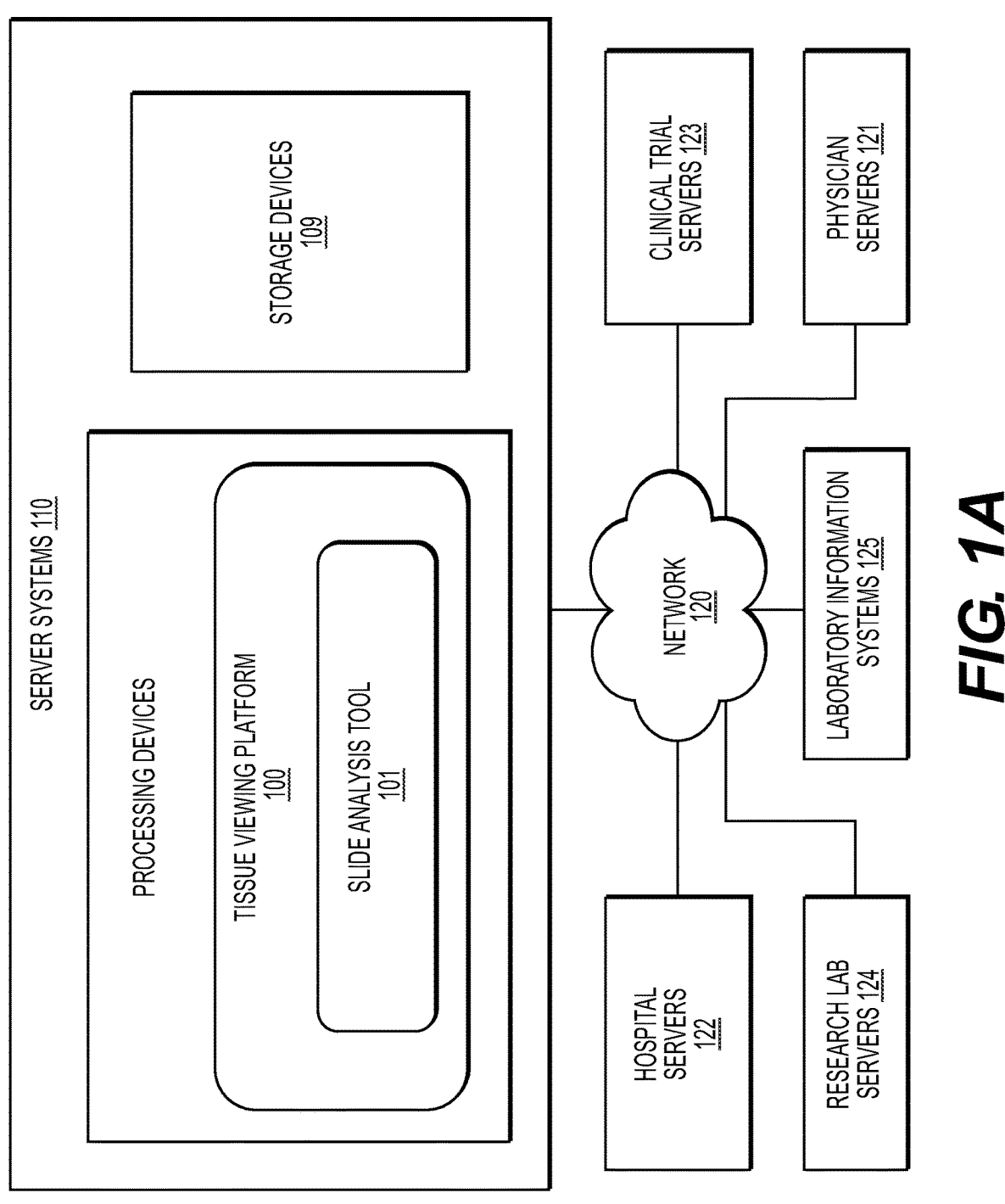
FIG. 1A illustrates an exemplary block diagram of a system and network to process electronic images using uncertainty estimations, according to an exemplary embodiment of the present disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

In some techniques, applications of artificial intelligence (AI) in medicine try to take inputs and outputs of the pre-existing test to replicate or predict the same outcomes of the pre-existing test using the same inputs. However, because the AI is trained to predict an outcome of the pre-existing test (e.g., outcomes of the pre-existing test are used as "ground truth" in training), rather than actual outcomes of patients, the AI system may possibly be more erroneous and/or removed from an actual outcome than the pre-existing test, which may have its own sensitivities, specificity, error profile, error characteristics, and/or or margin of error. Sensitivity may refer to and/or be based on the true positive rate or TPR, which may indicate a proportion of samples having a positive result that are genuinely positive.

In some situations, the AI system may not be better or more useful than the pre-existing test. Knowing error modes or margins of error in the AI system would facilitate determining and/or predicting when the AI system may fail and/or succeed within some small margin of error. Knowing when the AI system may fail (or succeed) may help in determining when an AI system may be useful and/or when using the pre-existing test may be more valuable than the pre-existing test, especially in view of the costs and/or time restraints of pre-existing tests.

Technical aspects disclosed herein may determine error modes or margins of an artificial intelligence (AI) system configured to make similar determinations as a pre-existing or traditional test. Technical aspects disclosed herein may provide determinations of when the AI system may be more useful than the pre-existing test and/or when the pre-existing test should be used instead of the AI system. For example, technical aspects disclosed herein may determine a certainty of an AI outcome, and when the certainty is below a threshold (e.g., a user-defined accuracy rate or difference for a certain percentage of data), determine that testing should fall back (or "reflex") to the pre-existing test on which the AI system is based.

Technical aspects disclosed herein may be used to determine certain subpopulations or other types of groups where accuracy of the AI system is lower and/or margins or error are higher than other populations. Such determinations may facilitate a determination that for those subpopulations or groups, testing should fall back or reflect to the pre-existing test on which the AI system is based. Technical aspects disclosed herein may be used to determine certain subpopulations or other types of groups where accuracy of the AI system is higher and/or margins or error are lower than other populations (e.g., higher than a predetermined accuracy, such as 80% or 90% accuracy, or higher than a predetermined confidence threshold, such as 0.8 or 0.9). Such determinations may facilitate a determination that, for those subpopulations or groups, the AI system has equivalence with (or is equivalent to) the pre-existing test on which it is based. The AI system may be configured to determine that, for populations where the accuracy is outside of the predetermined accuracy, a fallback test (e.g., the preexisting test) should be used.

Technical aspects disclosed herein may create multiple modes which an AI system may operate under, such as a safe mode and a "fallback" (or "reflex") mode which uses an alternative method. For instance, a pathologist's workflow for determining biomarker expression in a human epidermal growth factor receptor 2 (HER2) stain may be considered a test that takes in a whole slide image (e.g., a HER2 stained image) as input and makes a decision or determination based on the presence of HER2 expression and how strong the expression is or an intensity of the HER2 expression. In this case, the fallback mode of the AI system would be for the pathologist to analyze the HER2 stain and make a decision, rather than relying on determinations by the AI system. The fallback mode may be used when certainty of the AI system is low (e.g., below a certainty threshold) and/or error is high (e.g., above an error threshold), whereas the determinations by the AI system may be used where certainty of the AI system is high and/or error is low to reduce costs and testing times. Because HER2 stains may be very expensive and time consuming, using determinations by the AI system where certainty is high may reduce costs and time (e.g., lab processing and/or shipment costs and time).

The fallback modes may be extended to many tests in medicine, such as a polymerase chain reaction (PCR) test for coronavirus or COVID. In such a case, an AI system might be able to predict a PCR response with a high degree of confidence for most patients, but for some patients, the AI system may have a lower confidence or certainty. For most patients where the AI system has a high degree of confidence, using determinations from the AI system instead of the PCR test may save time and costs. For the patients where the AI system has a lower confidence, the AI system may fall back to the original PCR test that was developed.

Technical aspects disclosed herein may use built-in mechanisms of an AI system to determine a result of a fallback test and/or whether to fallback to a pre-existing test. Technical aspects disclosed herein may use an open set classifier and/or based on a consistency or variations among local features. Open set classification has the ability to decline to classify an input if the chance of incorrect labeling/output exceeds a threshold.

Figure 1B:
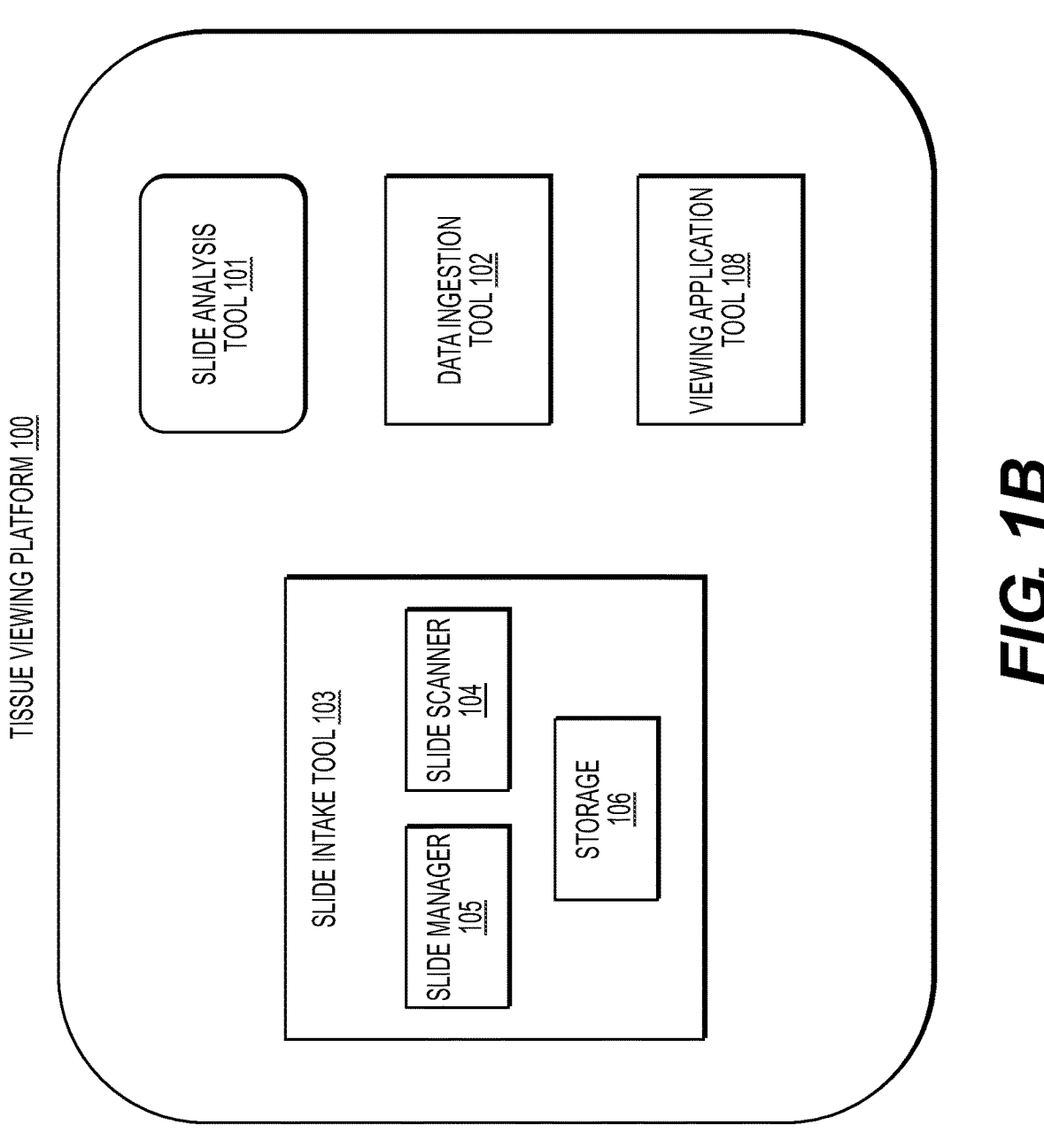
FIG. 1B illustrates an exemplary block diagram of a disease detection platform, according to an exemplary embodiment of the present disclosure.
Figure 1C:
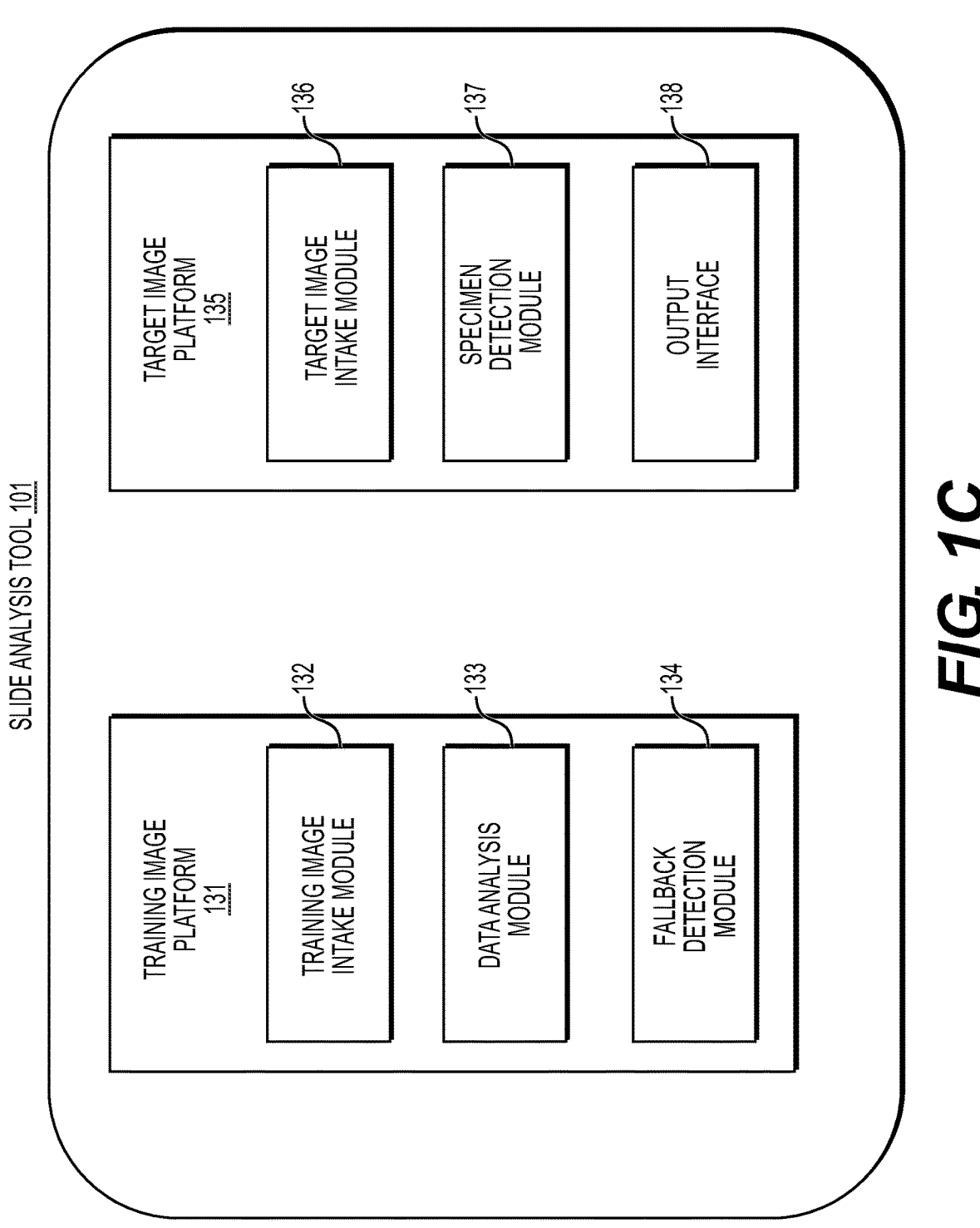
FIG. 1C illustrates an exemplary block diagram of a slide analysis tool, according to an exemplary embodiment of the present disclosure.

FIGS. 1A through 1C show a system and network to determine whether a fallback or alternative approach should be used instead of an AI prediction according to an exemplary embodiment of the present disclosure.

Specifically, FIG. 1A illustrates an electronic network 120 that may be connected to servers at hospitals, laboratories, and/or doctor's offices, etc. For example, physician servers 121, hospital servers 122, clinical trial servers 123, research lab servers 124, and/or laboratory information systems 125, etc., may each be connected to an electronic network 120, such as the Internet, through one or more computers, servers and/or handheld mobile devices. According to an exemplary embodiment of the present application, the electronic network 120 may also be connected to server systems 110, which may include processing devices that are configured to implement a disease detection platform 100, which includes a slide analysis tool 101 for determining specimen property or image property information pertaining to digital pathology image(s), and using machine learning to determine whether a disease or infectious agent is present, according to an exemplary embodiment of the present disclosure. The slide analysis tool 101 may allow for rapid evaluation of 'adequacy' in liquid-based tumor preparations, facilitate the diagnosis of liquid based tumor preparations (cytology, hematology/hematopathology), and predict molecular findings most likely to be found in various tumors detected by liquid-based preparations.

The physician servers 121, hospital servers 122, clinical trial servers 123, research lab servers 124 and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124 and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124 and/or laboratory information systems 125 refer to systems used by pathologists for reviewing the images of the slides. In hospital settings, tissue type information may be stored in a laboratory information system 125.

FIG. 1B illustrates an exemplary block diagram of a disease detection platform 100 for determining specimen property or image property information pertaining to digital pathology image(s), using machine learning. The disease detection platform 100 may include a slide analysis tool 101, a data ingestion tool 102, a slide intake tool 103, a slide scanner 104, a slide manager 105, a storage 106, and a viewing application tool 108.

The slide analysis tool 101, as described below, refers to a process and system for determining data variable property or health variable property information pertaining to digital pathology image(s). Machine learning may be used to classify an image, according to an exemplary embodiment. The slide analysis tool 101 may also predict future relationships, as described in the embodiments below.

The data ingestion tool 102 may facilitate a transfer of the digital pathology images to the various tools, modules, components, and devices that are used for classifying and processing the digital pathology images, according to an exemplary embodiment.

The slide intake tool 103 may scan pathology images and convert them into a digital form, according to an exemplary embodiment. The slides may be scanned with slide scanner 104, and the slide manager 105 may process the images on the slides into digitized pathology images and store the digitized images in storage 106.

The viewing application tool 108 may provide a user with a specimen property or image property information pertaining to digital pathology image(s), according to an exemplary embodiment. The information may be provided through various output interfaces (e.g., a screen, a monitor, a storage device and/or a web browser, etc.).

The slide analysis tool 101, and one or more of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools, and modules may be located on a device that may be connected to an electronic network such as the Internet or a cloud service provider, through one or more computers, servers and/or handheld mobile devices.

FIG. 1C illustrates an exemplary block diagram of a slide analysis tool 101, according to an exemplary embodiment of the present disclosure. The slide analysis tool 101 may include a training image platform 131 and/or a target image platform 135.

According to one embodiment, the training image platform 131 may include a training image intake module 132, a data analysis module 133, and a fallback detection module 134.

The training data platform 131, according to one embodiment, may create or receive training images that are used to train a machine learning model to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training image intake module 132 may create or receive a dataset comprising one or more training datasets corresponding to one or more health variables and/or one or more data variables. For example, the training datasets may be received from any one or any combination of the server systems 110, physician servers 121, hospital servers 122, clinical trial servers 123, research lab servers 124, and/or laboratory information systems 125. This dataset may be kept on a digital storage device. The data analysis module 133 may identify whether an area belongs to a region of interest or salient region, or to a background of a digitized image. The fallback detection module 134 may analyze digitized images and determine whether a region in the sample needs further analysis and/or whether a prediction associated with the sample is not certain. In some examples, the fallback detection module 134 may detect a subpopulation to which the sample belongs and/or whether the sample belongs to a certain subpopulation, and the fallback detection module 134 may alternatively be referred to as a subpopulation detection module. The identification of such may trigger an alert to a user.

According to one embodiment, the target image platform 135 may include a target image intake module 136, a specimen detection module 137, and an output interface 138. The target image platform 135 may receive a target image and apply the machine learning model to the received target image to determine a characteristic of a target data set. For example, the target data may be received from any one or any combination of the server systems 110, physician servers 121, hospital servers 122, clinical trial servers 123, research lab servers 124, and/or laboratory information systems 125. The target image intake module 136 may receive a target dataset corresponding to a target health variable or a data variable. Specimen detection module 137 may apply the machine learning model to the target dataset to determine a characteristic of the target health variable or a data variable. For example, the specimen detection module 137 may detect a trend of the target relationship. The specimen detection module 137 may also apply the machine learning model to the target dataset to determine a quality score for the target dataset. Further, the specimen detection module 137 may apply the machine learning model to the target images to determine whether a target element is present in a determined relationship.

The output interface 138 may be used to output information about the target data and the determined relationship (e.g., to a screen, monitor, storage device, web browser, etc.). The output interface 138 may display determinations by the fallback detection module 134, an indication of whether a fallback method should be used, a recommendation as to a fallback method, a detected subpopulation, a detected certainty level, a visualization (e.g., tissue or 2D map) depicting a consistency of findings in a received image, etc.

Figure 2:
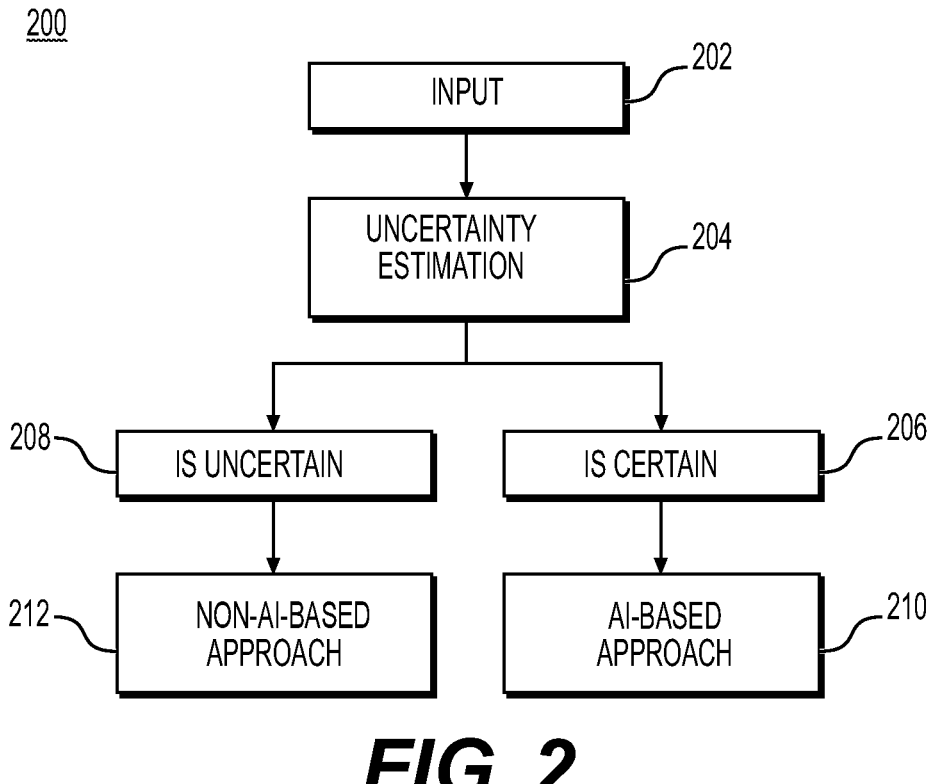
FIG. 2 illustrates a method of determining whether to use an AI or a non-AI based approach, according to an exemplary embodiment of the present disclosure.

Referring to FIG. 2, aspects disclosed herein may be used to determine whether to use an AI output for a test (e.g., AI diagnostic prediction) or whether to "reflex" (or "fall back" to a non-AI test on which the AI output is based (e.g., physical diagnostic test). An AI system 200 may include receiving an input 202 (e.g., patient information, disease information, a whole slide image, etc.) and determining an outcome or prediction (e.g., diagnosis). Alternatively or in addition thereto, an AI-determined outcome or prediction may be received as input 202.

The AI system 200 may determine, from the input 202, a certainty or uncertainty estimation (e.g., level, score, percentage, etc.) 204 of the determined (or received) outcome or prediction. The certainty estimation may indicate a certainty that a predetermined AI system or method (e.g., AI diagnostic test) will provide an accurate prediction. The AI system 200 may use the uncertainty estimation 204 to determine whether the outcome or prediction is certain 206 or is uncertain 208.

For example, the AI system 200 may compare the uncertainty estimation 204 to a threshold, and if the uncertainty estimation 204 is at or above the threshold (or is not below the threshold), the AI system 200 may determine that the outcome or prediction is certain 206, and if the uncertainty estimation 204 is below the threshold (or is not at or above the threshold), the AI system 200 may determine that the outcome or prediction is uncertain 208.

If the AI system 200 determines that the outcome or prediction is certain 206, then the AI system 200 may recommend proceeding and/or using the determined outcome or prediction. If the AI system 200 determines that the outcome or prediction is uncertain 208, then the AI system 200 may determine that an alternative method (e.g., fallback method or diagnosis test, or another AI system) and/or a non-AI approach 212 should be used to determine the outcome or prediction. The alternative method/non-AI approach 212 may be a pre-existing method, such as a pre-existing test, on which the AI system 200 is based and/or is meant to simulate.

Determining the uncertainty estimation 204 may include determining whether a patient or other information associated with the input 202 belongs to a subpopulation for which the AI system has a certain accuracy level. Determining whether a patient or other information associated with the input 202 belongs to the subpopulation may include using an open set classifier (for example, as described with reference to FIGS. 3-4) and/or based on a determined variance of local features in received images (for example, as described with reference to FIGS. 5-6). If the AI system 200 determines that the patient belongs to the subpopulation, then the AI system 200 may determine that the outcome or prediction is certain 206, and use the AI-based approach 210. If the AI system 200 determines that the patient does not belong to the subpopulation, then the AI system 200 may determine that the outcome or prediction is uncertain 208, and that the non-AI-based approach 212 should be used.

Using Open-Set Classifiers to Determine Fallback

Open set classification may be used to identify a test method, or whether an AI system should fallback back to an alternative method (e.g., pre-existing test) due to uncertainty in the output. Open set classification may endow a classifier with the ability to express uncertainty and/or to indicate that a result is not known. With open set classification, a model (e.g., a Convolutional Neural Network or CNN, Recurrent Neural Network or RNN, transformer, etc.) may predict labels, such as a presence of cancer, a presence of a large tumor, etc., in addition to an unknown class, which may correspond to uncertainty or not knowing. An unknown classification may indicate that an input (e.g., whole slide image or WSI, or portion thereof) is inside and/or outside of a subpopulation for which the AI system may have more or less accuracy or confidence and may result in the AI system determining that the fall back method (e.g., the preexisting test) should be used.

Figure 3:
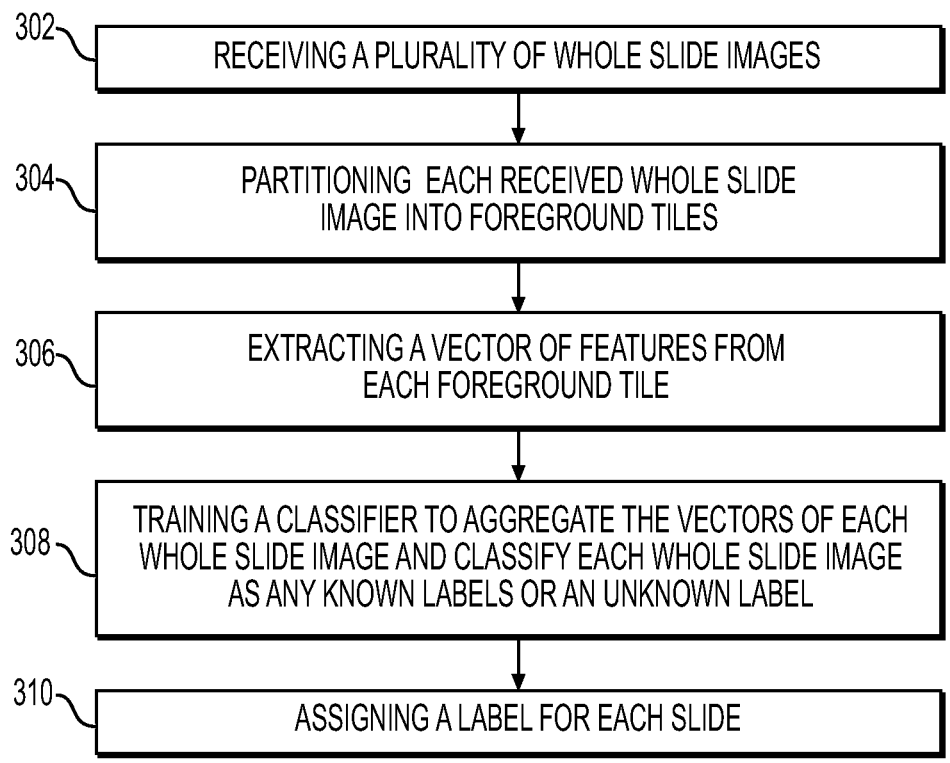
FIG. 3 illustrates a method of training a model or classifier to determine whether to use an AI-based approach, according to an exemplary embodiment of the present disclosure.

Referring to FIG. 3, a method 300 of training the AI system may include a step 302 of receiving a plurality of images (e.g., electronic or digital images or whole slide images (WSIs)) into electronic or digital storage (e.g., cloud-based storage, hard disk, RAM, etc.) The images may be associated with a plurality of samples and/or a plurality of patients.

The method 300 may include a step 304 of breaking or partitioning each received image into foreground tiles, which may be square or rectangular foreground tile tissue images. Step 304 of breaking each received image may include using thresholding based on a variance of pixels in a tile to identify whether those pixels are foreground, using Otsu's method, comparing tile pixel values to a reference foreground distribution, etc.

The method 300 may include a step 306 of extracting a vector of features from each foreground tile to create a tile-level feature vector. Step 306 of extracting the vector of features may include using a range of techniques such as hand-engineered features (e.g., scale invariant feature transform (SIFT) descriptors, oriented FAST and rotated BRIEF (ORB) descriptors, rotation invariant feature transform (RIFT) descriptors, speeded up robust features (SURF) descriptors, etc.), pre-trained CNN embeddings using supervised learning, pre-trained CNN embeddings using self-supervised learning techniques, pre-trained transformer neural network features, etc.

The method 300 may include a step 308 of training a model or a classifier (e.g., Convolutional Neural Network or CNN, Recurrent Neural Network or RNN, transformer, etc.) to aggregate the tile-level feature vectors of each image (e.g., WSI) and classify the image as any known labels or an unknown label. Step 308 of training the model or classifier may include using open-set regularization methods (e.g., Tempered Mixup, out-of-distribution detector for neural networks (ODIN), OpenMax, One-class SVM, etc.) such as those described in "Are open set classification methods effective on large-scale datasets?" by Ryne Roady, Tyler L. Hayes, Ronald Kemker, Ayesha Gonzales, and Christopher Kanan, published Sep. 4, 2020, the entire contents of which are incorporated by reference herein.

The method 300 may include a step 310 of assigning, for each slide, a label. Step 310 of assigning the label may include using any sort of decision rule such as an argmax function or operation of all outputs. The label may relate to a certainty determination (e.g., unknown label), a subpopulation, an identified salient feature, a determination or diagnosis, etc.

Referring to FIG. 4, a method 400 of using a trained model, classifier and/or AI system may include a step 402 of receiving at least one image (e.g., digital or electronic image or a whole slide image (WSI)) into electronic storage (e.g., cloud-based storage, hard disk, RAM, etc.) The received image may be associated with a sample of a patient. The method 400 may include a step 404 of breaking or partitioning the received image and/or slide of the image into foreground tiles, which may be square, or some other shape, foreground tile tissue images. Step 402 of breaking the image may include using thresholding based on a variance of pixels in a tile to identify whether the pixels are foreground, using Otsu's method, comparing the tile pixel values to a reference foreground distribution etc.

The method 400 may include a step 406 of extracting a vector of features from each foreground tile. Step 406 of extracting the vector of features to create a tile-level feature vector for each received image. Step 406 may include using hand-engineered features (e.g., SIFT, ORB, RIFT, SURF, etc. descriptors), pre-trained CNN embeddings using supervised learning, pre-trained CNN embeddings using self-supervised learning techniques, pre-trained transformer neural network features, etc.

The method 400 may include a step 408 of determining a classified label. Determining the classified label may include running the tile-level feature vector of the received image through a trained model and/or a classifier (e.g., an aggregation classifier) to determine the classified label. For example, step 408 of determining the classified label may include determining a subpopulation of a patient associated with the received image, a disease, an uncertainty level of the disease and/or the label, etc.

The method 400 may include a step 410 of determining whether an alternative or fallback (e.g., pre-existing) method should be used based on the determined classified label. If, in step 408, the image is classified as a known label, then step 410 may include determining that using this known label as the output of the classifier is safe or acceptable, and/or that an alternative or fallback method is not necessary. If, however, the image is classified as an unknown label in step 408, then step 410 may include determining that an alternative or fallback method should be used, determining the alternative method, and/or initiating or triggering the alternative method.

The method 400 may include a step 412 of outputting the classified label (e.g., to a storage device or a display). Step 412 may also include outputting other determinations by the trained classifier such as an accuracy or confidence level, a recommendation that an alternative method (e.g., pre-existing test and/or a non-AI based approach) should be used, etc. The alternative method may be a pre-existing method, such as a pre-existing test, on which the AI system is based and/or is meant to simulate. For example, the alternative methods described herein may comprise a manual test conducted by a pathologist and/or other physician.

Fallback Test Based on Local Features

Alternatively or in addition to using a classifier, local features (e.g., of a WSI) may be used to identify whether an AI system should fallback back to a pre-existing test due to uncertainty in an output. The WSI may be broken up, partitioned, or divided into tiles, and a model, classifier, or AI system may make an aggregate prediction based on all tiles (e.g., a value between −1 and 1). The AI system may further run a statistical analysis on tiles individually to determine consistency and/or variance in features, and may further determine whether a WSI belongs to a subpopulation for which determinations by the AI system are above a certain accuracy and/or based on whether the WSI is associated with a sample or patient that is outside of the subpopulation.

For example, a higher degree of consistency among the tiles (e.g., tiles in a same area and/or adjacent tiles indicate a presence of cancer) may indicate that the WSI falls within the subpopulation. A lower degree of consistency among the tiles (e.g., indications of presence of cancer are spread apart or sparse and/or in nonadjacent tiles) may indicate that the WSI falls outside of the subpopulation. These local features may be output as a 2D or 3D map and may be used to assess confidence.

Referring to FIG. 5, a method 500 of training the AI system may include a step 502 of receiving a plurality of (e.g., set of) images such as electronic or digital images or WSIs into electronic storage (e.g., cloud-based storage, hard disk, RAM, etc.) The method may include a step 504 of breaking or partitioning each received image into foreground tiles, which may be square foreground tissue tile images. Step 504 of partitioning each image may include using thresholding based on a variance of pixels in a tile to identify whether those pixels are foreground, using Otsu's method, comparing the tile pixel values to a reference foreground distribution, etc.

The method 500 may include a step 506 of extracting a vector of features from each foreground tile to create a tile-level feature vector for each image. Step 506 of extracting a vector of features may include using a range of techniques, including hand-engineered features (e.g., SIFT, ORB, RIFT, SURF, etc. descriptors), pre-trained CNN embeddings using supervised learning, pre-trained CNN embeddings using self-supervised learning techniques, pre-trained transformer neural network features, etc.

The method 500 may include a step 508 of training a model or a classifier (CNN, RNN, transformer, etc.) to aggregate the tile-level feature vectors of each image and classify the image (e.g., as any known label or an unknown label). The step 508 may include a step 510 of assigning, for each slide, a label. Step 510 of assigning the label may include using any sort of decision rule such as an argmax operation or function of all outputs. The label may relate to a subpopulation assignment or classification, identified features, a variance in features, or other characteristics.

The method 500 may include a step 512 of determining whether information or features in local regions of each image are consistent and/or determining a consistency of information or features across each image. Step 512 may include performing and/or running a statistical analysis (e.g., variance of tile features, entropy of tile features, etc.) using local tile-level features to determine whether the information contained in local regions is consistent, such as variance of tile features, entropy of tile features, spatial coordinate determinations, etc. Based on the consistency, step 512 may include determining a subpopulation for each image. Based on the subpopulations among all images, step 512 may further include determining accuracy levels and/or confidence thresholds for each image. Steps 508 and/or 512 may include determining local feature information for each tile and comparing the feature information across all tiles.

In some examples, the method 500 might not include classifying and/or using a classifier. For example, steps 508 through 512 may include training a model to identify and/or analyze inconsistencies, variance in features, and/or inconsistent multiple morphologies present, and/or to recommend (or perform) a further analysis based on the identified (e.g., number of) analyzed inconsistencies, etc. In addition, steps 508 through 512 may include highlighting each identified morphology, feature, etc. (e.g., on a tissue map or other visualization) for review by a pathologist and/or for further analysis.

Referring to FIG. 6, a method 600 of using a trained model, classifier and/or AI system may include a step 602 of receiving at least one image (e.g., WSI) into electronic storage (e.g., cloud-based storage, hard disk, RAM, etc.) The method 600 may include a step 604 of breaking or partitioning each received image into foreground tiles, which may be square foreground tissue tile images. Step 604 of partitioning each received image may include using thresholding based on a variance of pixels in a tile to identify whether those pixels they are foreground, using Otsu's method, comparing the tile pixel values to a reference foreground distribution, etc.

The method 600 may include a step 606 of extracting a vector of features from each foreground tile to create a tile-level feature vector for each received image. Step 606 of extracting a vector of features may include using a range of techniques, including hand-engineered features (e.g., SIFT, ORB, RIFT, SURF, etc. Descriptors), pre-trained CNN embeddings using supervised learning, pre-trained CNN embeddings using self-supervised learning techniques, pre-trained transformer neural network features, etc.

The method 600 may include a step 608 of determining a classified label for the received image. Step 608 of determining the classified label may include running the tile-level feature vectors of each image through a trained model, classifier, or system (e.g., an aggregation classifier) to determine the classified label. The classified label may indicate or be associated with a subpopulation, a certainty level, etc.

The method 600 may include a step 610 of determining whether an alternative or fallback method should be used. Step 610 may include using the determined classified label and/or local tile-level feature information to determine if the AI system should fall back to the alternative method.

Step 610 may include determining a consistency of features in local regions and/or determining a consistency of features across the received image based on the classified label and/or vector. Step 610 may include running or performing a statistical analysis on each partitioned tile of the image to determine the consistency and/or variance in features and/or feature information. Step 610 may include determining a subpopulation for the received image.

Step 610 may further include determining whether the image belongs to and/or is associated with (or alternatively, is outside of or is not associated with) a group, category, or a subpopulation for which determinations by the AI system are above or below a certain accuracy. If, in step 610, the consistency of features and/or feature information among tiles is higher than a predetermined consistency threshold, step 610 may include determining that the image belongs to a subpopulation for which determinations by the AI system are above a certain accuracy and determining that an alternative method is not necessary.

If, in step 610, the consistency of features and/or feature information among tiles is lower than the predetermined consistency threshold, step 610 may include determining that the image belongs to a subpopulation for which determinations by the AI system are below a certain accuracy and/or determining that the image does not belong to the subpopulation where determinations by the AI system are above a certain accuracy, and determining that an alternative method should be used. In such a case, step 610 may include determining the alternative method to be used and/or initiating the alternative method.

The method 600 may include a step 612 of outputting the determination of whether an alternative method should be used and/or other determinations, such as an accuracy or confidence level, whether the image is in a subpopulation, a recommendation of an alternative method and/or a non-AI based approach to be used, etc. Step 612 may also include outputting local features (e.g., identified in step 612) as a 2D or 3D map and/or outputting a determined subpopulation.

In some examples, the method 600 might not include classifying and/or using a classifier. For example, steps 608 through 612 may include identifying and/or analyzing inconsistencies, variance in features, and/or inconsistent multiple morphologies present, and/or recommending (or performing) a further analysis based on the identified (e.g., number of) analyzed inconsistencies, etc. In addition, steps 608 through 612 may include highlighting each identified morphology, feature, etc. (e.g., on a tissue map or other visualization) for review by a pathologist and/or for further analysis.

Fallback Test in Biomarker Screening

Certain biomarker tests may already have a margin of error, which may be significant. When using an AI system to reproduce a pre-existing test, the AI system may have errors that may or may not overlap with errors of the pre-existing test. In training the AI system to reproduce results of the pre-existing test, test results from the pre-existing test may be considered as "ground truth" and, therefore, the AI results may be measured against the pre-existing test's prediction of some outcome rather than the actual outcome itself. Showing equivalency with the pre-existing test may require matching certain metrics that the pre-existing test has with the actual outcome.

Pre-existing tests are often costly and time consuming. For example, polymerase chain reaction (PCR) tests may take three days, and some stains (e.g., HER2 stains) may take days or weeks to process due to, for example, shipments of slides. In addition, these pre-existing tests may be costly and incur significant lab fees, shipment fees, etc. Outcomes predicted by AI, however, may take a matter of seconds or minutes. Where the AI results are equivalent or close to equivalent with the pre-existing test, using AI is advantageous.

Therefore, a subpopulation of the data that can show equivalence with the pre-existing test, and a subpopulation of the data that cannot show equivalents, may be considered. The latter subpopulation would, in this case, mean that the AI system should "fallback" or "reflex" to an alternative method (such as the pre-existing test or another non-AI approach) such that, overall, correspondence to actual outcome data may be maintained.

"Equivalence" may be user-defined based on predetermined or prescribed thresholds (such as confidence levels). For example, some users may consider that the AI system is equivalent with the pre-existing test for a given subpopulation based on a confidence threshold of above 0.8 or 0.9, above an accuracy of 80% or 90%, below an error rate of 10% or 20%, etc. These thresholds may be input into the AI system and/or changed base on a user's preference (e.g., 80% accuracy versus 90% accuracy).

Adjustments in subpopulations may be made based on user-defined accuracy levels. For example, if a user (e.g., clinician, institution, etc.) desires 90% accuracy, but an AI system has an 80% accuracy on all of the data, then technical aspects disclosed herein may be used to determine subpopulations for which the AI system has higher or lower accuracy. For example, the AI system may determine subpopulations for which the AI system has lower accuracy and/or for which the AI system would recommend using a fallback method, and remove these subpopulations from the data. Alternatively, the AI system may determine subpopulations for which the AI system has higher accuracy and/or for which the AI system would not recommend using a fallback method, and remove all other subpopulations from the data. Once those subpopulations are removed, the accuracy of the AI system may increase when just the remaining subpopulations are considered.

If the user wants to change the accuracy to, for example, 95% (e.g., based on different needs, different clinic standards, etc.), then more subpopulations having lower accuracy may be removed from a primary subpopulation where the AI system outcome is used, and the fallback test would be used for those removed subpopulations. In a case where the user desires 80% accuracy, and the AI system has an 80% accuracy on all of the data, then the subpopulation for which the AI system has equivalence may include everything, and certain subpopulations might not need to be removed.

Uncertainty may be determined based on thresholds, which, as previously described, may be set by a user or alternatively determined by the AI system. For example, a user may desire 90% accuracy for 80% of data. Technical aspects disclosed herein may predict when to fallback to an alternative method from built-in mechanisms of an AI system.

The AI system may be trained to determine and/or recognize subpopulations based on received images and to determine certainty levels or confidence thresholds associated with subpopulations. The certainty level may indicate a certainty that a predetermined AI system or method will provide a correct or accurate prediction, output, or result. The certainty level may be based on a comparison of a performance by the predetermined AI system with a comparison of the fallback or alternative method. The AI system may be used to determine a subpopulation of a received image and/or whether a received image belongs to a certain subpopulation and, based on the determination, recommend whether to proceed with an AI prediction or outcome or to fallback to an alternative method.

Figure 7:
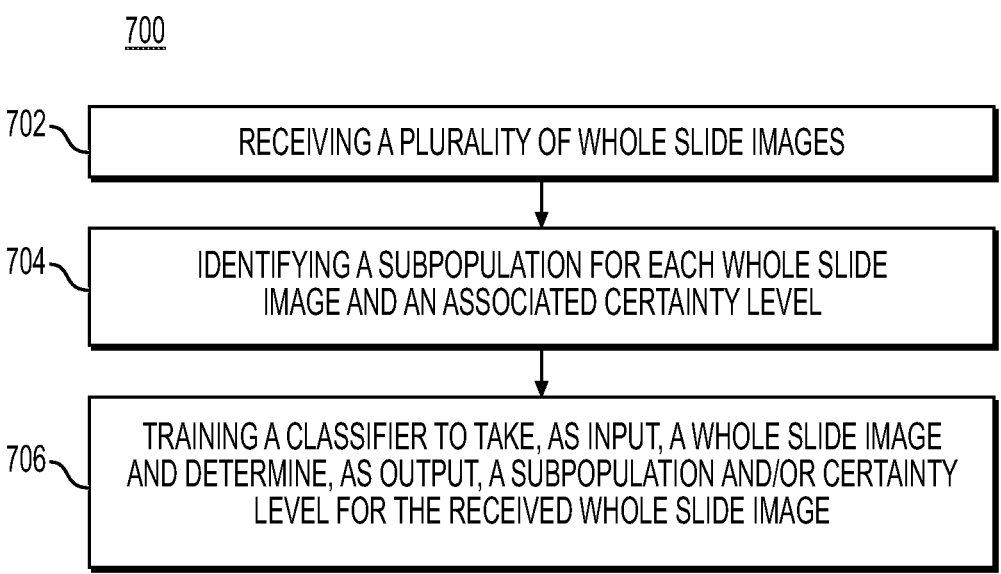
FIG. 7 illustrates a method of training a model to determine whether to use an AI-based approach based on an identified subpopulation, according to an exemplary embodiment of the present disclosure.

Referring to FIG. 7, a method 700 of training an AI system may include a step 702 of receiving a plurality of images (e.g., electronic or digital images or whole slide images (WSIs)) into electronic or digital storage (e.g., cloud-based storage, hard disk, RAM, etc.) The images may be associated with a plurality of samples and/or a plurality of patients.

The method 700 may include a step 704 of identifying a subpopulation for each whole slide image and an associated certainty level and/or result of a prediction (e.g., a diagnosis and/or a result of an AI-based test). The certainty level may indicate a certainty that a predetermined AI system or method will provide an accurate prediction. Identifying the subpopulation may include receiving the subpopulation and associated certainty level from annotations, as additional information, and/or using the methods described with reference to FIG. 3 and/or FIG. 5. In some examples, identifying the associated certainty level may include receiving outcome information of the prediction (e.g., whether the prediction, diagnosis, result, etc. was correct) and determining a certainty level for each identified subpopulation.

The method 700 may include a step of training a model or classifier to take, as input, an image (e.g., electronic or digital images or whole slide images (WSIs)) and identify or determine, as output, a subpopulation and/or a certainty level (e.g., a certainty level associated with the subpopulation) for the received whole slide image. The certainty level may indicate a certainty that a predetermined AI system or method will provide an accurate prediction.

Referring to FIG. 8, a method 800 of using and/or modifying the AI system may include a step 802 of receiving, into electronic or digital storage, an input related to a predetermined or desired accuracy or confidence threshold. Receiving in step 802 may include retrieving the predetermined confidence threshold from storage and/or from an input by a user (e.g., clinician). The confidence threshold may be based on a certainty level associated with an alternative method (e.g., to show equivalency with the alternative method).

The method 800 may include a step 804 of receiving a plurality of images (e.g., electronic or digital images or whole slide images (WSIs)) into electronic or digital storage (e.g., cloud-based storage, hard disk, RAM, etc.).

The method 800 may include a step 806 of running a trained model or classifier (e.g., a model trained using the method 300, a model trained using the method 500, and/or a model trained using the method 700) to identify or determine a subpopulation and/or an associated certainty level (e.g., a certainty level associated with the determined subpopulation) for the received image. The certainty level may indicate a certainty that a predetermined AI system or method will provide an accurate prediction. Step 806 may include determining whether the received image and/or a sample associated with the received image is part of one or more predetermined subpopulations (e.g., subpopulations for which a certainty level is above the determined confidence threshold).

The method 800 may include a step 808 of comparing a certainty level associated with the subpopulation (e.g., a determined certainty level and/or a certainty level previously stored or determined for the subpopulation) to the received predetermined confidence threshold.

The method 800 may include a step 810 of determining whether an alternative method should be used based on the comparison. If the determined certainty level is less than the predetermined confidence threshold, then step 810 may include determining that the alternative method should be used. If the determined certainty level is equal to or greater than the predetermined confidence threshold, then step 810 may include determining that an AI-based prediction or determination should be used.

The method 800 may include a step 812 of storing or filtering the received image and/or associated data based on the comparison and/or the determination. For example, step 812 may include storing images and associated data for images determined to be in subpopulations associated with certainty levels that are greater than or equal to the received confidence threshold. Step 812 may include removing, from a set of images, images and associated data for images determined to be in subpopulations associated with certainty levels that are less than the confidence threshold and/or that are outside the subpopulations associated with certainty levels that are greater than or equal to the received confidence threshold. Step 812 may include creating an image set and/or data set for images where an AI approach may be relied on.

Figure 9:
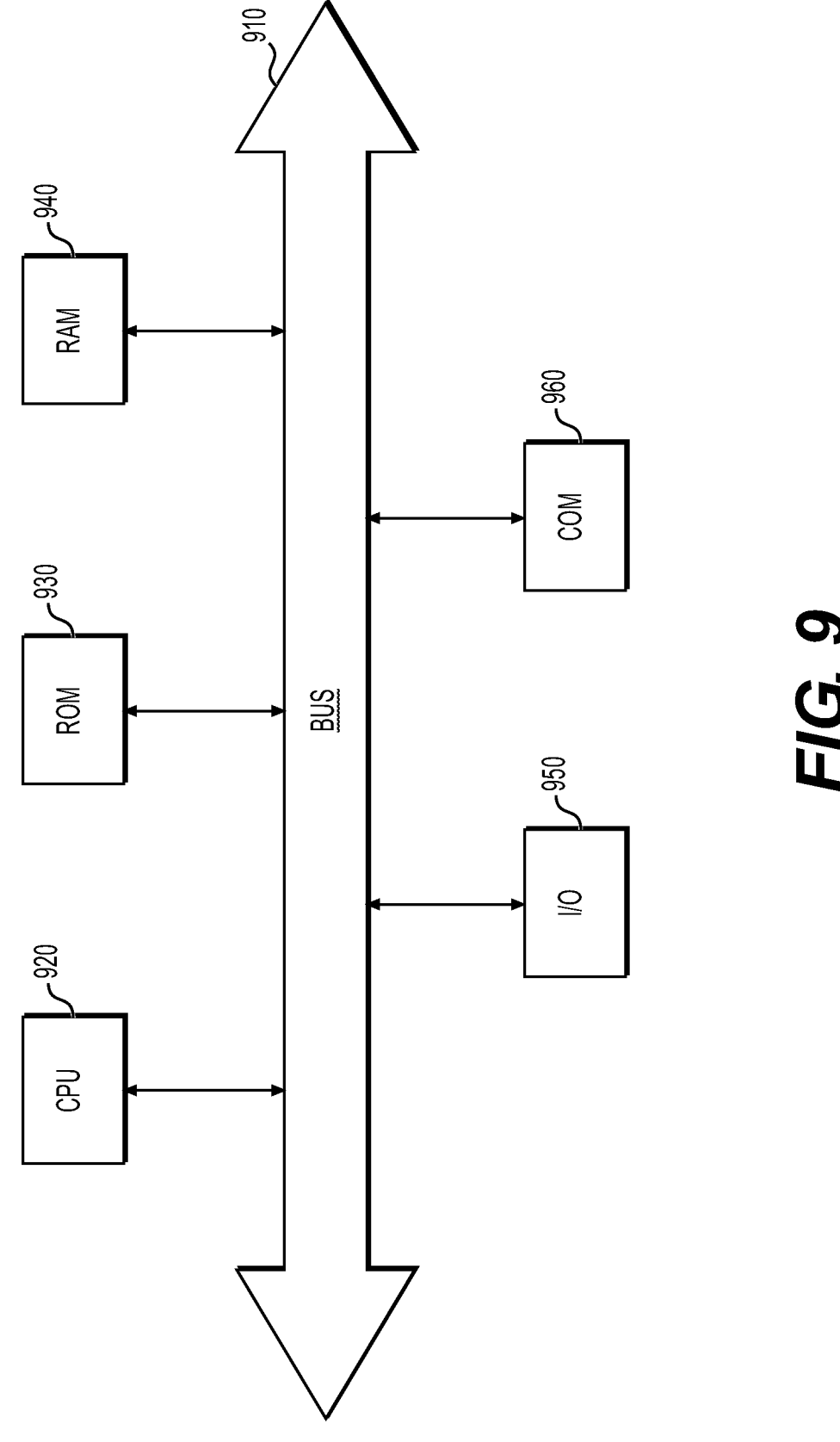
FIG. 9 depicts an example of a computing device that may execute techniques presented herein, according to one or more embodiments.

Referring to FIG. 9, a device 900 may include a central processing unit (CPU) 920. CPU 920 may be any type of processing device including, for example, any type of special purpose or a general-purpose microprocessor device. As will be appreciated by persons skilled in the relevant art, CPU 920 also may be a single processor in a multi-core/multiprocessor system, such system operating alone, or in a cluster of computing devices operating in a cluster or server farm. CPU 920 may be connected to a data communication infrastructure 910, for example a bus, message queue, network, or multi-core message-passing scheme.

Device 900 may also include a main memory 940, for example, random access memory (RAM), and may also include a secondary memory 930. Secondary memory 930, e.g., a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 930 may include similar means for allowing computer programs or other instructions to be loaded into device 900. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 900.

Device 900 also may include a communications interface ("COM") 960. Communications interface 960 allows software and data to be transferred between device 900 and external devices. Communications interface 960 may include a model, a network interface (such as an Ethernet card), a communications, a PCMCIA slot and card, or the like. Software and data transferred via communications interface 960 may in the form of signals, which may be electronic, electromagnetic, optical or other signals capable of being received by communications interface 960. These signals may be provided to communications interface 960 via a communications path of device 900, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 900 may also include input and output ports 950 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention may be apparent to those skilled in the art from consideration of the specification and practice of the invention disclosed herein. It is intended that the specification and examples be considered as exemplary only.

What is claimed is:

1. A computer-implemented method of determining whether to use an artificial intelligence (AI) assisted prediction using an AI system, the method comprising:

receiving, by one or more processors of the AI system, one or more electronic slide images associated with a pathology specimen; and providing, by the one or more processors, the one or more electronic slide images to a machine learning model, the machine learning model trained to:

classify the one or more electronic slide images to determine a certainty level corresponding to a certainty that a predetermined AI system will provide an accurate prediction for the pathology specimen;

determine whether the certainty level equals or exceeds a predetermined confidence threshold; and upon determining that the certainty level does not equal or exceed a predetermined confidence threshold, output a determination to not use the predetermined AI system for the AI assisted prediction for the pathology specimen.

2. The method of claim 1, wherein running the machine learning model to determine the certainty level includes identifying a subpopulation of the pathology specimen.

3. The method of claim 1, wherein running the machine learning model to determine whether the certainty level equals or exceeds a predetermined confidence threshold includes running a trained classifier to determine a classified label, the classified label indicating at least one of a subpopulation or whether the pathology specimen is outside of one or more predetermined subpopulations.

4. The method of claim 3, wherein running the classifier to determine the classified label includes:

partitioning the received electronic slide images into a plurality of foreground tiles;

extracting a vector of features from each foreground tile; and running each vector through the trained classifier to determine the classified label.

5. The method of claim 1, wherein running the machine learning model to determine whether the certainty level equals or exceeds a predetermined confidence threshold includes detecting one or more features in the received electronic slide images and determining a consistency of the detected one or more features.

6. The method of claim 5, wherein detecting the one or more features in the received electronic slide images and determining the consistency includes:

partitioning the received electronic slide images into a plurality of foreground tiles;

extracting a vector of the detected one or more features from each foreground tile;

determining local feature information for each foreground tile; and analyzing, using statistical analysis, the determined local feature information for all foreground tiles to determine the consistency.

7. The method of claim 5, further comprising outputting a visualization of the detected one or more features and/or the determined consistency.

8. The method of claim 1, wherein running the machine learning model to determine the certainty level includes:

partitioning the received electronic slide images into a plurality of foreground tiles;

extracting a vector of features from each foreground tile; and running each extracted vector through the machine learning model to determine at least one of: (i) a subpopulation for the pathology specimen, or (ii) an unknown label indicating that the pathology specimen is outside one or more predetermined subpopulations.

9. The method of claim 1, wherein determining to not use the predetermined AI system includes:

detecting that the pathology specimen is outside one or more predetermined subpopulations.

10. The method of claim 9, further comprising determining that an alternative method should be used, wherein the predetermined AI system was trained using results from the alternative method as ground truth.

11. The method of claim 1, further comprising determining the predetermined confidence threshold based on a user input.

12. The method of claim 1, wherein the certainty level is based on a comparison of a performance by the predetermined AI system with a comparison of an alternative method.

13. The method of claim 1, wherein the predetermined confidence threshold is based on a certainty level associated with an alternative method.

14. The method of claim 1, wherein the predetermined AI system is configured to detect a presence and/or an intensity of HER2 expression.

15. The method of claim 1, wherein the predetermined AI system is configured to predict a response to a polymerase chain reaction (PCR) test.

16. The method of claim 1, further comprising outputting a recommendation for an alternative method, wherein the alternative method is configured to make a same type of prediction as the predetermined AI system.

17. The method of claim 1, further comprising storing or removing the received electronic slide images, based on whether the pathology specimen belongs to one or more predetermined subpopulations, to create a data set based on one or more electronic images for which the certainty level equals or exceeds the predetermined confidence threshold.

18. A system for determining whether to use an artificial intelligence (AI) assisted prediction, the system comprising:

at least one memory storing instructions; and at least one processor configured to execute the instructions to perform operations comprising:

receiving, by the at least one processor, one or more electronic slide images associated with a pathology specimen; and providing, by the at least one processor, the one or more electronic slide images to a machine learning model, the machine learning model trained to:

classify the one or more electronic slide images to determine a certainty level corresponding to a certainty that a predetermined AI system will provide an accurate prediction for the pathology specimen;

determine whether the certainty level equals or exceeds a predetermined confidence threshold; and upon determining that the certainty level does not equal or exceed a predetermined confidence threshold, output a determination to not use the predetermined AI system for the AI assisted prediction for the pathology specimen.

19. The system of claim 18, wherein running the machine learning model to determine the certainty level includes identifying a subpopulation of the pathology specimen.

20. A non-transitory computer-readable medium storing instructions that, when executed by a processor, perform a method for determining whether to use an artificial intelligence (AI) assisted prediction, the method comprising:

receiving, by the processor, one or more electronic slide images associated with a pathology specimen; and providing, by the processor, the one or more electronic slide images to a machine learning model, the machine learning model trained to:

classify the one or more electronic slide images to determine a certainty level corresponding to a certainty that a predetermined AI system will provide an accurate prediction for the pathology specimen;

determine whether the certainty level equals or exceeds a predetermined confidence threshold; and upon determining that the certainty level does not equal or exceed a predetermined confidence threshold, output a determination to not use the predetermined AI system for the AI assisted prediction for the pathology specimen.

\* \* \* \* \*